(12) United States Patent
Lv et al.

(10) Patent No.: US 12,422,342 B2
(45) Date of Patent: Sep. 23, 2025

(54) PREPARATION METHOD OF MICRO-NANOFLUIDIC MODEL OF TRIPLE-MEDIUM CARBONATE RESERVOIR

(71) Applicant: CHINA UNIVERSITY OF PETROLEUM-BEIJING, Beijing (CN)

(72) Inventors: Qichao Lv, Beijing (CN); Rong Zheng, Beijing (CN); Chenggang Xian, Beijing (CN); Honglei Zhan, Beijing (CN); Juan Zhang, Beijing (CN); Tongke Zhou, Beijing (CN); Abdolhossein Hemmati-Sarapardeh, Beijing (CN); Tingting Yi, Beijing (CN); Saeid Norouzi Apourvari, Beijing (CN)

(73) Assignee: CHINA UNIVERSITY OF PETROLEUM—BEIJING, Beijing (CN)

( * ) Notice: Subject to any disclaimer, the term of this patent is extended or adjusted under 35 U.S.C. 154(b) by 0 days.

(21) Appl. No.: 18/976,628

(22) Filed: Dec. 11, 2024

(65) Prior Publication Data

US 2025/0251322 A1 Aug. 7, 2025

(30) Foreign Application Priority Data

Feb. 2, 2024 (CN) .......................... 202410154853.4

(51) Int. Cl.
*G01N 1/00* (2006.01)
*G01N 1/32* (2006.01)
(Continued)

(52) U.S. Cl.
CPC ............. *G01N 1/32* (2013.01); *G01N 15/082* (2013.01); *G01N 33/24* (2013.01); *E21B 49/088* (2013.01)

(58) Field of Classification Search
CPC ........... G01N 1/00; G01N 1/32; G01N 15/00; G01N 15/08; G01N 15/082; G01N 33/24; E21B 49/088
See application file for complete search history.

(56) References Cited

U.S. PATENT DOCUMENTS

2016/0363691 A1  12/2016  Hu et al.

FOREIGN PATENT DOCUMENTS

| CN | 102053026 A | 5/2011 |
| CN | 102866043 A | 1/2013 |

(Continued)

OTHER PUBLICATIONS

CN-112927592 Machine Translation (Year: 2021).*

(Continued)

*Primary Examiner* — Nguyen Q. Ha
(74) *Attorney, Agent, or Firm* — Jacob M. Ward; Ward Law Office LLC

(57) ABSTRACT

A preparation method of a micro-nanofluidic model of triple-medium carbonate reservoir includes the following steps: obtaining a cave structure, a fracture structure and a pore structure of a carbonate rock, and preparing a first mask, a second mask and a third mask respectively; forming a photoresist layer on a glass substrate, and subjecting the photoresist layer to an exposure treatment and an etching treatment through the first mask, the second mask and the third mask sequentially, and then subjecting to a washing treatment, to obtain a first intermediate model; fitting the etched side of the first intermediate model with a glass cover, and subjecting to a bonding treatment, to obtain a second intermediate model; introducing a first solution, a second solution and a third solution into the second intermediate model sequentially to form a calcium carbonate nanocrys- (Continued)

talline layer and to obtain the micro-nanofluidic model of triple-medium carbonate reservoir.

9 Claims, 7 Drawing Sheets

(51) Int. Cl.
*G01N 15/08* (2006.01)
*G01N 33/24* (2006.01)
*E21B 49/08* (2006.01)

(56) References Cited

FOREIGN PATENT DOCUMENTS

| CN | 105089657 | A |   | 11/2015 |           |
|----|-----------|---|---|---------|-----------|
| CN | 105178926 | A |   | 12/2015 |           |
| CN | 107204288 | A |   | 9/2017  |           |
| CN | 112598986 | A |   | 4/2021  |           |
| CN | 112927592 | A | * | 6/2021  |           |
| CN | 114427997 | A |   | 5/2022  |           |
| CN | 116861716 | A |   | 10/2023 |           |
| CN | 117368050 | A |   | 1/2024  |           |
| CN | 118329725 | A | * | 7/2024  | G01N 29/07 |

OTHER PUBLICATIONS

CN-118329725-A (Year: 2024).*
Lv, Qichao, et al., "Visualization study of CO2-EOR in carbonate reservoirs using 2.5D heterogeneous micromodels for CCUS", Fuel, vol. 330, Aug. 12, 2022, 125533, Elsevier, https://doi.org/10.1016/j.fuel.2022.125533.

* cited by examiner

PREPARATION METHOD OF MICRO-NANOFLUIDIC MODEL OF TRIPLE-MEDIUM CARBONATE RESERVOIR

CROSS-REFERENCE TO RELATED APPLICATION

The present application claims priority to Chinese Patent Application No. 202410154853.4, filed on Feb. 2, 2024. The aforementioned patent application is hereby incorporated by reference in its entirety.

TECHNICAL FIELD

The present disclosure relates to the technical field of underground carbon sequestration technology and oil and gas field development, and in particular, to a preparation method of a micro-nanofluidic model of triple-medium carbonate reservoir.

BACKGROUND

Carbonate oil and gas reserve occupies an important position in oil and gas resource pattern of the world, accounting for about 60%. The development of carbonate reservoir can provide not only hydrocarbon energy, but also storage space for carbon dioxide. Therefore, carbonate reservoir is a suitable choice for oil displacement utilization and geological storage of carbon dioxide. However, complex diagenetic, reaction, deposition and deformation processes produce a multi-scale heterogeneity of the formation and lead to complex flow behavior in porous media, which makes carbonate reservoir difficult to be developed. In addition, carbonate reservoirs may also contain multi-scale natural fracture networks, which constitute complex cross-flow flow paths in the reservoir. Variation in matrix structure and fracture network communication is a main reason why triple-medium carbonate reservoirs exhibit multiple flow behaviors, which leads to large uncertainty in predicting carbon dioxide sequestration distribution and oil and gas recovery.

Traditional rock model cannot observe the complex flow behaviors and oil displacement process in porous media. The microfluidic model, which is a device with a transparently connected porous network, can directly observe the complex fluid flow behaviors occurring inside. Since the 1950s, a variety of two-dimensional micromodels have been developed to study flow and transport phenomena in porous media. These studies are based on direct observations of pore-scale and/or macro-scale fluid structures, visualization of flow fields, and characterization of matrix-fluid interactions. These studies have important guiding significance for petroleum engineering, geological engineering and environmental engineering.

When carrying out an oil flooding experiment of the micro-nanofluidic model, an important requirement is to invert structure characteristics of three-dimensional porous media of rock to the micro-nanofluidic model, so that the microstructure of the micro-nanofluidic model can represent the three-dimensional characteristics of real rock. The existing micro-nanofluidic models mainly use array structures of regular models, which cannot fully simulate the three-dimensional structural characteristics of real rock; some of the micro-nanofluidic models refer to the characteristics of two-dimensional rock slices, which cannot reflect the three-dimensional communication of porous media. The existing microfluidic design ignores the three-dimensional structural characteristics of real rock, which seriously restricts the application and development of micro-nanofluidic model in the petroleum field.

SUMMARY

The present disclosure provides a preparation method of a micro-nanofluidic model of triple-medium carbonate reservoir, and this method can obtain the micro-nanofluidic model of triple-medium carbonate reservoir by restoration of triple-medium structure of carbonate rock and continuous etching and in-situ modification, enabling to simulate real microstructural features of carbonate rock.

In a first aspect of the present disclosure, there is provided a preparation method of a micro-nanofluidic model of triple-medium carbonate reservoir, including the following steps: obtaining a cave structure, a fracture structure and a pore structure of a carbonate rock, and preparing a first mask, a second mask and a third mask respectively, where the first mask has the cave structure, the second mask has the fracture structure and the cave structure, and the third mask has the cave structure, the fracture structure and the pore structure; forming a photoresist layer on a glass substrate, and subjecting the photoresist layer to an exposure treatment and an etching treatment by the first mask, the second mask and the third mask sequentially, and then subjecting to a washing treatment, to obtain a first intermediate model; fitting the etched side of the first intermediate model with a glass cover, and subjecting to a bonding treatment, to obtain a second intermediate model; introducing a first solution, a second solution and a third solution into the second intermediate model sequentially to form a calcium carbonate nanocrystalline layer and obtain the micro-nanofluidic model of triple-medium carbonate reservoir, where the first solution includes N-(trimethoxysilylpropyl)ethylenediamine triacetic acid sodium salt, and the second solution includes $Ca^{2+}$, and the third solution includes $CO_3^{2-}$.

The preparation method as described above further includes the following steps: introducing crude oil and water into the micro-nanofluidic model of triple-medium carbonate reservoir sequentially to undergo flushing treatment, and subjecting to an aging and drying treatment, to change the model wettability from water-wet characteristic to oil-wet characteristic; or, introducing a paraffin solution, crude oil and water into the micro-nanofluidic model of triple-medium carbonate reservoir sequentially to undergo a flushing treatment, and subjecting to an aging and drying treatment, to change the model wettability from water-wet characteristic to mixed-wet characteristic or oil-wet characteristic.

In the preparation method as described above, a process of obtaining the cave structure, fracture structure and pore structure of the carbonate rock includes the following steps: selecting a triple-medium carbonate rock, washing oil and drying, to obtain a rock sample in cylindrical shape; subjecting the rock sample to scanning image to obtain the cave structure and fracture structure of the carbonate rock; obtaining the pore structure of the rock sample by a thin section and a scanning electron microscopy.

The preparation method as described above, before applying photoresist on the glass substrate, further includes the following steps: placing the glass substrate in a solution including a surfactant to undergo an ultrasonic treatment.

In the preparation method as described above, the photoresist layer includes at least one layer; and in one implementation, the photoresist layer includes two layers.

In the preparation method as described above, the etching treatment is at least one of wet etching and inductively coupled plasma etching.

In the preparation method, the forming the photoresist layer on the glass substrate, and subjecting the photoresist layer to the exposure treatment and the etching treatment by the first mask, the second mask and the third mask sequentially, and then subjecting to the washing treatment, to obtain the first intermediate model includes: forming a first photoresist layer on the glass substrate, and subjecting the first photoresist layer to a first exposure treatment and a first etching treatment through the first mask, and then a first washing treatment, to obtain a first etched model; forming a second photoresist layer on the first etched model, and subjecting the second photoresist layer to a second exposure treatment and a second etching treatment through the second mask, and then a second washing treatment, to obtain a second etched model; forming a third photoresist layer on the second etched model, and subjecting the third photoresist layer to a third exposure treatment and a third etching treatment through the third mask, and then a third washing treatment, to obtain the first intermediate model; where the first etching treatment and the second etching treatment each are wet etching, and the third etching treatment is inductively coupled plasma etching method.

The preparation method as described above includes stacking the etched side of the first intermediate model with the glass cover to obtain a model to be bonded, placing the model to be bonded between two graphite sheets, and placing a steel plate or a corundum on a side of the two graphite sheets away from the model to be bonded, and then horizontally placing into a muffle furnace to undergo the bonding treatment; where the bonding treatment has a temperature of 400-700° C. and time of 4-12 h.

The preparation method as described above further includes the following steps: subjecting to a punching treatment at both ends of the first intermediate model to form an injection inlet and a collection outlet, where the first solution, the second solution and the third solution are injected sequentially through the injection inlet, the collection outlet is to collect the solution flowing in from the injection inlet.

In the preparation method as described above, a thickness of the calcium carbonate nanocrystalline layer is 0.5-4 μm.

The implementation of the present disclosure has at least the following beneficial effects.

(1) The preparation method of the micro-nanofluidic model of triple-medium carbonate reservoir provided by the present disclosure can simulate the triple-medium structure inside the carbonate rock, i.e., the cave structure, the fracture structure and the pore structure, improving the accuracy of simulating the flow of the real carbonate reservoir, and being conducive to the study of the relationship among pores, fractures and caves in the carbonate rock.

(2) The present disclosure makes etching depth of the triple-medium structure controllable through continuous etching, which solves the problem that the depth cannot be controlled in the prior art; and in the present disclosure different etching depths of structures reflect different fluid conductivity of the triple-medium structure in a vertical direction, which improves the accuracy of simulating the flow of real carbonate reservoir.

(3) Fluidic models in the prior art usually use glass or other smooth materials to prepare microchannels, and these materials are greatly different in surface roughness from an actual carbonate reservoir, and show water-wet characteristic whereas in the present disclosure, a structure with calcium carbonate nanocrystalline layer is formed in microchannels, which can more accurately simulate the natural roughness of surface of the carbonate reservoir, thereby providing a more real model for studying the flow of oil and gas in the reservoir. Formation of the calcium carbonate nanocrystalline layer on surfaces of the microchannels in the present disclosure enables the wettability of the model to be closer to an actual carbonate reservoir, and thus allows a more accurate study of flow behaviors of oil and gas in this condition. The preparation method of micro-nanofluidic model of triple-medium carbonate reservoir forms the calcium carbonate nanocrystalline layer in microchannels by in-situ modification, which truly reflects the surface roughness of carbonate reservoir and also simulates the wetting characteristics of oil wettability, which is of great significance for deep study of flow mechanism of oil and gas in carbonate reservoir and improvement of recovery efficiency of oil and gas.

(4) The preparation method of the present disclosure is simple and low cost, and the micro-nanofluidic model of triple-medium carbonate reservoir prepared by the preparation method can withstand the harsh conditions of high temperature (300° C.) and high pressure (70 MPa), has a wide range of application, and is helpful to study the transport process of matter and the flow behavior of oil, gas and water in porous media of carbonate reservoir under different solid-liquid and solid-liquid-gas conditions, and the model can be reused.

The present disclosure shows remarkable uniqueness in the field of underground carbon sequestration, and focuses on large-scale $CO_2$ storage by using geological structures such as carbonate rocks. By adopting the micro-nanofluidic model of triple-medium carbonate reservoir, the present disclosure can simulate complex properties, pore characteristics and heterogeneity of the underground rock, and realize the visual study of $CO_2$ interface phenomenon and multi-phase flow behavior in underground porous media after $CO_2$ injection. This technology can not only efficiently monitor and evaluate the utilization and sequestration effect of $CO_2$, but also provide important guidance for numerical simulation optimization and on-site operation of large-scale geological sequestration, so as to optimize the application of carbon sequestration technology in underground.

DESCRIPTION OF EMBODIMENTS

In order to make the purpose, technical solution and advantages more clear, the technical solutions in the examples of the present disclosure will be described clearly and completely in combination with examples of the present disclosure. Obviously, the examples described are some of examples of the present disclosure, not all examples. Based on the examples in the present disclosure, all other examples obtained by those skilled in the art without creative work fall within the protection scope of the present disclosure.

Figure 1:
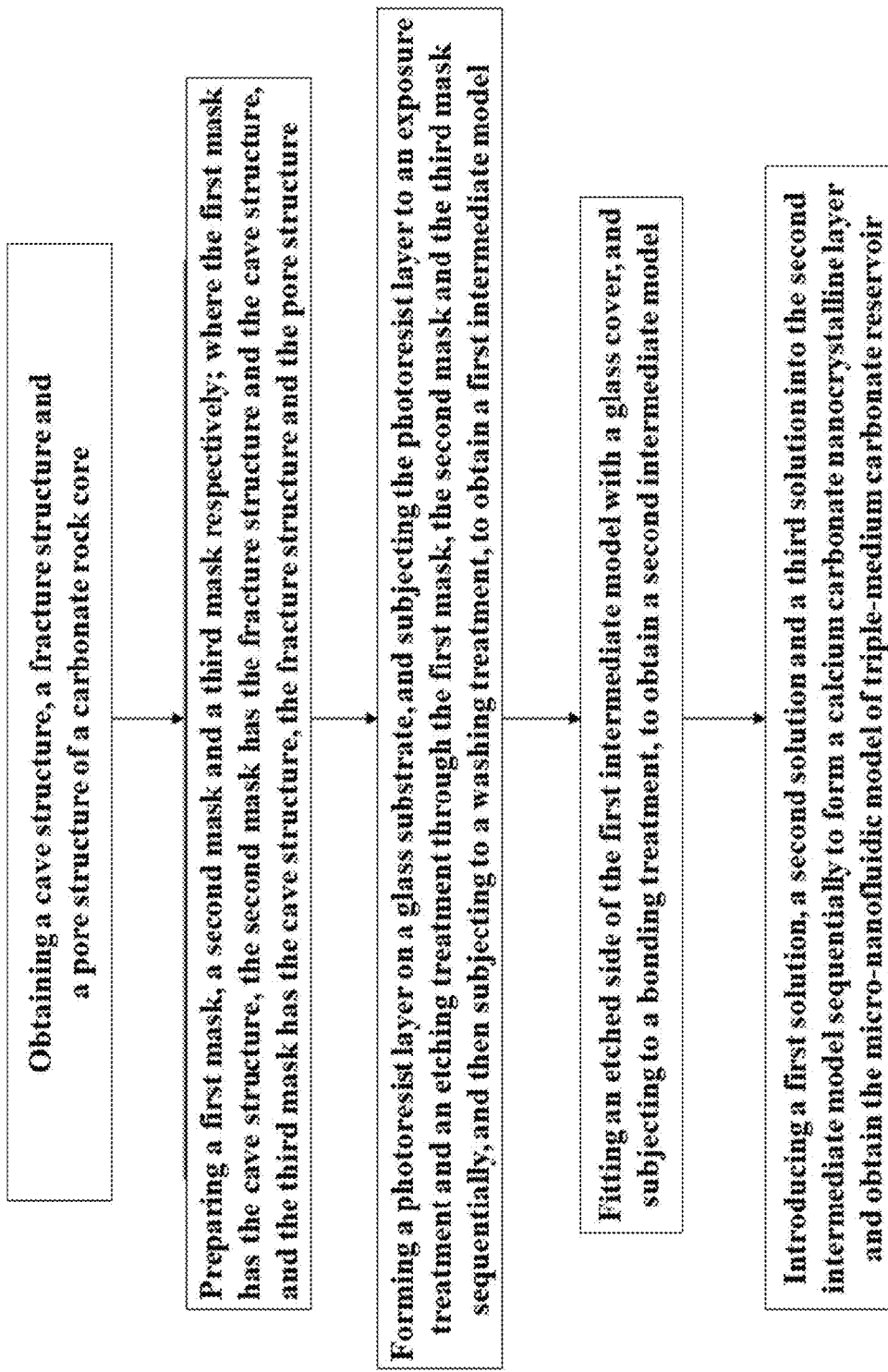
FIG. 1 is a flowchart of a preparation method of micro-nanofluidic model of triple-medium carbonate reservoir in an embodiment of the present disclosure.

As shown in FIG. 1, a first aspect of the present disclosure provides a preparation method of a micro-nanofluidic model of triple-medium carbonate reservoir, including the following steps: obtaining cave structure, fracture structure and pore structure of a carbonate rock, and preparing a first mask, a second mask and a third mask respectively, where the first mask has the cave structure, the second mask has the fracture structure and the cave structure, and the third mask has the cave structure, the fracture structure and the pore structure; forming a photoresist layer on a glass substrate, and subjecting the photoresist layer to an exposure treatment and an etching treatment through the first mask, the second mask and the third mask sequentially, and washing, to obtain a first intermediate model; fitting the etched side of the first intermediate model with a glass cover, and subjecting to a bonding treatment, to obtain a second intermediate model; introducing a first solution, a second solution and a third solution into the second intermediate model sequentially to form a calcium carbonate nanocrystalline layer, to obtain the micro-nanofluidic model of triple-medium carbonate reservoir, where the first solution includes N-(trimethoxysilylpropyl)ethylenediamine triacetic acid sodium salt, and the second solution includes $Ca^{2+}$, and the third solution includes $CO_3^{2-}$.

It should be noted that a diameter of the pore structure of the present disclosure is less than 100 µm, an opening of the fracture structure is greater than or equal to 100 µm, and a diameter of the cave structure is greater than 2 mm.

After obtaining the cave structure, fracture structure and pore structure of the carbonate rock, the obtained cave structure, fracture structure and pore structure are drawn to generate mask layouts that can be recognized by lithography equipment (specifically calibrated to an image resolution of 1 µm per pixel). According to differences of the layouts, the mask layouts are divided into a first mask pattern, a second mask pattern and a third mask pattern, where the first mask pattern includes a pattern of the cave structure, the second mask pattern includes patterns of the fracture structure and the cave structure, and the third mask pattern includes patterns of the cave structure, fracture structure and pore structure.

It should be noted that after obtaining pore structure, fracture structure and cave structure from micron to nanometer scale, it is also necessary to construct the communication of pore structure, fracture structure and cave structure, in order to obtain the second mask pattern with both fracture structure pattern and cave structure pattern and the third mask pattern with cave structure pattern, fracture structure pattern and pore structure pattern.

The patterns on the first mask pattern, the second mask pattern and the third mask pattern are transferred to a mask material to form the first mask, the second mask and the third mask, so that the first mask has the cave structure, the second mask has the fracture structure and the cave structure, and the third mask has the cave structure, the fracture structure and the pore structure. Where, the preparation of the first mask, the second mask and the third mask can be carried out by conventional lithography equipment in the field.

A photoresist is coated on the glass substrate so that a photoresist layer is formed on the glass substrate and is laminated on the glass substrate. Using a photochemical reaction of the photoresist, mask patterns are transferred from masks to the photoresist layer in an exposure treatment, as parts of the photoresist layer that are exposed to a developer will be dissolved under action of the developer, and thus parts of the glass substrate will be exposed to be dissolved and other parts of the glass substrate will still be coated with the remaining photoresist layer that are masked thus retained. A following etching treatment essentially etches the exposed part of the glass substrate, thus the parts of the glass substrate not protected by the remaining photoresist layer will be corroded and dissolved to a certain depth under action of an etching solution, forming a pattern area, while the remaining glass substrate protected by the remaining photoresist layer will be retained in its original state, and thus can also be called non-pattern area. Then, the remaining photoresist layer is removed by washing treatment, and etched patterns formed with respect to the masks are formed in the glass substrate.

Where, the glass substrate has largest and opposite two functional surfaces, and the photoresist layer is arranged on one of the two functional surfaces. The photoresist can be a conventional photoresist in the field, as long as it is ensured that the photoresist is resistant to the etching treatment and that the photoresist does not detach from the surface of the glass substrate.

Because there is the cave structure on the first mask, the fracture structure and the cave structure on the second mask, and the cave structure, the fracture structure and the pore structure on the third mask, in the process of exposure treatment and etching treatment through the first mask, the second mask and the third mask sequentially, it may be that a first exposure treatment and a first etching treatment can be first carried out through the first mask, then a second exposure treatment and a second etching treatment are carried out through the second mask, and finally a third exposure treatment and a third etching treatment are carried out through the third mask. That is, a position corresponding to the cave structure on the glass substrate is actually etched three times, a position of the fracture structure is actually etched twice, and a position of the pore structure is actually etched once. At this time, etching depth at the position of the cave structure>etching depth at the position of the fracture structure>etching depth at the position of the pore structure. The reason for this setting of the present disclosure is that pores, fractures and caves have obviously different pore size, length and shape, and also different storage capacity and permeability, and selecting different etching depths for different porous media can further strengthen the difference in permeability of different media, which is helpful to better reflect the topological relationship, communication and fluid conductivity of different porous media structures in the micro-nanofluidic model of triple-medium carbonate reservoir.

The washing treatment is mainly using washing solution to remove residual photoresist layer, etching solution and other impurities, and the first intermediate model is finally obtained after the washing treatment.

Where the functional surface of the glass substrate with photoresist layer is subjected to etching treatment to form the cave structure, fracture structure and pore structure with a certain etching depth, and the functional surface with these structures constitutes the etched side of the first intermediate model.

Fitting the etched side of the first intermediate model (shown in FIGS. 6 and 7, having a side with a pattern area) with a glass cover can also be understood that the first intermediate model is stacked with the glass cover, and the side having the pattern area of the first intermediate model faces a surface of the glass cover. Because the pattern area of the first intermediate model has a certain depth, it is essential that the non-pattern (non-etched) area of the first intermediate model is fitted in contact with the surface of the glass cover. Where the glass cover has the same size as the glass substrate.

The first intermediate model and the glass cover, which have been fitted together, are subjected to a bonding treatment so that the non-pattern area (non-etched area) of the first intermediate model is closely bonded with the glass cover to form a whole and thus form the second intermediate model. At this time, the pattern area in the first intermediate model and the glass cover form a channel of the second intermediate model.

Figure 8:
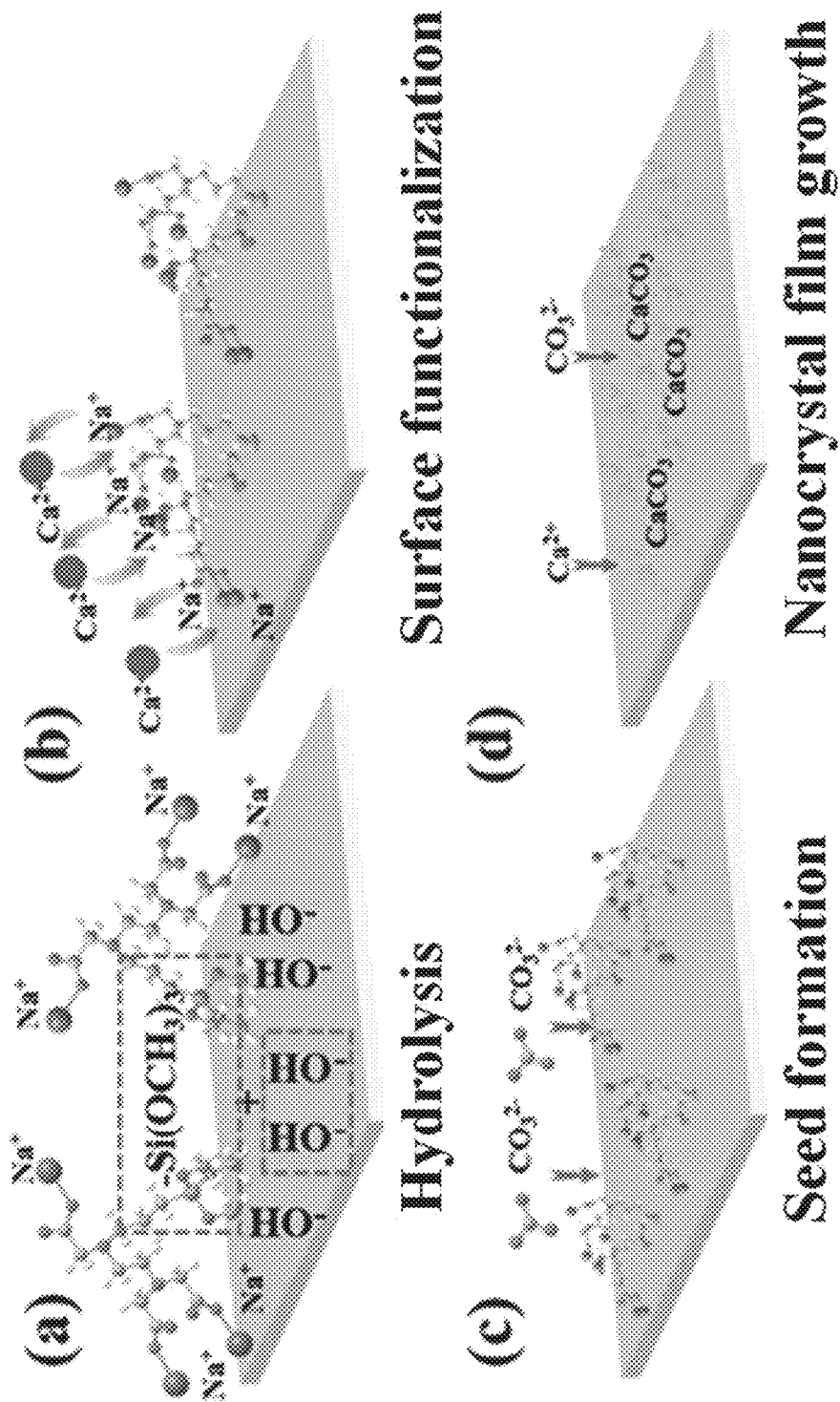
FIG. 8 is a perspective view of the reaction process of forming calcium carbonate nanocrystalline layer by in-situ modification in an embodiment of the present disclosure.

A first solution, a second solution and a third solution are sequentially introduced into the second intermediate model. In essence, the first solution, the second solution and the third solution are sequentially introduced into the microchannel of the second intermediate model, that is, a calcium carbonate nanocrystalline layer is formed on the surface of the microchannel, where the first solution contains N-(trimethoxysilylpropyl)ethylenediamine triacetic acid sodium salt, and the second solution contains $Ca^{2+}$, and the third solution contains $CO_3^{2-}$. Since the surface of the glass substrate contains a large number of hydroxyl groups, as shown in (a) of FIG. 8, the surface of the microchannel of the second intermediate model also contains a large amount of hydroxyl groups; after introducing the first solution, methoxy in N-(trimethoxysilylpropyl) ethylenediamine triacetic acid sodium salt undergoes hydrolysis reaction to form a silanol, and the silanol undergoes a condensation reaction with a carboxylic acid group to form an oligomer, the hydroxyl groups on the oligomer combines with the hydroxyl group on the second intermediate model through a hydrogen bond, and then form a covalent bonds by dehydration condensation to obtain the second intermediate model with $COO^-$ group on the surface; after introducing the second solution, as shown in (b) of FIG. 8, the $COO^-$ group combines with $Ca^{2+}$ to form a precursor layer; after introducing the third solution, as shown in (c) and (d) of FIG. 8, $Ca^{2+}$ combines with $CO_3^{2-}$ to form the $CaCO_3$ nanocrystalline layer. The $CaCO_3$ nanocrystalline layer can be stably attached to the channel of the second intermediate model, thereby forming a microchannel with uneven surface, and $CaCO_3$ nanocrystalline can be randomly arranged on the surface of the microchannel through in-situ synthesis, to restore a rough surface of a real carbonate reservoir and reflect the surface wettability of the real carbonate reservoir, which is conducive to better simulation of a real carbonate reservoir environment.

According to the research of the present disclosure, the method can simulate real microstructure characteristics of carbonate rocks. This is because that, in one aspect, through continuous etching, the present disclosure can not only simulate the triple-medium structure, i.e., cave structure, fracture structure and pore structure, in carbonate, but also reflect through etching depth the simulation difference of vertical fluid conductivity of the triple-medium structure, so as to improve the accuracy of simulating flow of the real carbonate reservoir; in another aspect, the present disclosure forms a microchannel with a calcium carbonate nanocrystalline layer by an in-situ modification method, and thus can truly reflect the roughness and wetting characteristics of the surface of the carbonate reservoir. Therefore, the preparation method provided by the present disclosure can simulate the real microstructure characteristics of carbonate rock through the above two aspects, and improve the accuracy.

The present disclosure, by the method of solution flushing the microchannel in the micro-nanofluidic model of triple-medium carbonate reservoir, allows flexible wetting modification of the microchannel in the model can be flexibly to form a water-wet, oil-wet or mixed-wet model, so that the microchannel in the model is more consistent with the oil and gas transport channel in the actual reservoir. In some embodiments, the following steps are also included: sequentially introducing crude oil and water into the micro-nanofluidic model of triple-medium carbonate reservoir to undergo a flushing treatment, and subjecting to a drying treatment, to change the model wettability from water-wet characteristic to oil-wet characteristic; or, introducing a paraffin solution, a crude oil and water into the micro-nanofluidic model of triple-medium carbonate reservoir to undergo a flushing treatment, and subjecting to a drying treatment, to change the model wettability from water-wet characteristic to mixed-wet characteristic or oil-wet characteristic.

Where, in the process of the flushing treatment, the above liquids are injected into the microchannel in the model sequentially. Through the above flushing treatment, the wetting modification of the model is realized. After flushing treatment, it is necessary to carry out the drying treatment to eliminate the influence of residual liquid.

In a specific implementation process of the present disclosure, a crude oil is injected into the micro-nanofluidic model of triple-medium carbonate reservoir, then the model is put into an oven at 60° C. and taken out after 24 h; the injected crude oil is rinsed with clean water, and then the surface of the obtained model becomes an oil-wet surface, which reflects a water-wet characteristic of the reservoir. In addition, it may also be that a melted paraffin solution is injected into the micro-nanofluidic model of triple-medium carbonate reservoir to block some of the microchannels of the model, and then the crude oil is injected into the model and the model is put into the oven and taken out after 24 h of aging, residual paraffin and crude oil in the model are cleaned with clean water, then the surface of the obtained model is transformed into a mixed-wet surface.

The present disclosure does not limit the obtaining mode of the triple-medium structure, which can be obtained by using a conventional method in the field. For example, the triple-medium structure can be carved out using a desktop CNC milling machine, or obtained by a lithography technology. In some embodiments, a process of obtaining the cave structure, the fracture structure and the pore structure of a carbonate rock includes the following steps: selecting a triple-medium carbonate rock, washing oil and drying, to prepare a cylindrical rock sample; subjecting the rock sample to scanning image to obtain a cave structure and a fracture structure of the carbonate rock; obtaining a pore structure of the rock sample, i.e., a pore structure of the carbonate rock, by a thin section and a scanning electron microscopy.

Furthermore, the triple-medium carbonate rock can be selected and prepared into two cylindrical rock samples, which are a first section rock sample and a second section rock sample, respectively; the first section rock sample is subjected to scanning image to obtain the cave structure and the fracture structure of the carbonate rock; the pore structure of the second section rock sample is obtained by the thin section and scanning electron microscopy.

In the present disclosure, it further comprises scanning a communication relationship in the rock sample by using a scanning electron microscopy, and reconstructing a communication structure obtained from scanning to distinguish a pore-cave-fracture triple-medium structure, specifically to obtain morphological characteristics, size parameters and communication relationships of the pore structure, the cave structure and the fracture structure with high-definition in high resolution.

The influence of impurities on the surface of the glass substrate on the model can be avoided by pretreating the glass substrate. In some embodiments, before applying photoresist on the glass substrate, the following steps are further included: placing the glass substrate in a solution containing a surfactant to undergo an ultrasonic treatment. The ultrasonic treatment can be for 5 min, and the impurities on the surface of glass substrate can be removed by the ultrasonic treatment to avoid the influence of the impurities on the subsequent model fabrication.

The present disclosure does not limit the number of photoresist layers, which can be adjusted according to actual situations. In some embodiments, the photoresist layer is at least one layer; in one implementation, the photoresist layer is two layers. When the photoresist layer is two layers, it may be that a first photoresist layer is coated on the glass substrate first, and a second photoresist layer is coated after heating, and then a two-layer photoresist layer is formed after heating.

The present disclosure does not limit specific operation steps of the etching treatment, which can be such as chemical etching, physical etching, or physicochemical etching. The etching treatment is to etch part of the exposed glass substrate, so as to transfer the patterns on the masks to the glass substrate. In some embodiments, the etching treatment is at least one of wet etching and inductively coupled plasma etching.

Where the wet etching is a traditional etching method, in which part of the exposed glass substrate is removed by a chemical reaction with a chemical reagent. The wet etching is simple, has a low equipment requirement, is easy to realize mass production, and has good etching selectivity. However, the wet etching is difficult to accurately control the pattern. The inductively coupled plasma etching is utilizing a discharge gas and part of the exposed glass substrate to undergo an ion chemical reaction to obtain molecules or molecular groups to generate volatile reaction products to achieve etching. The inductively coupled plasma etching has good etching selectivity and high etching rate, and can control the etching accuracy, but has low efficiency.

The present disclosure selects different etching methods according to the structural characteristics of the triple-medium, which is conducive to better simulation of the real carbonate reservoir. In some embodiments, a first photoresist layer is formed on the glass substrate, and the first photoresist layer is subjected to a first exposure treatment and a first etching treatment through the first mask, and subjected to a first washing treatment, to obtain a first etched model; a second photoresist layer is formed on the first etched model, and the second photoresist layer is subjected to a second exposure treatment and a second etching treatment through the second mask, and subjected to a second washing treatment, to obtain a second etched model; a third photoresist layer is formed on the second etched model, and the third photoresist layer is subjected to a third exposure treatment and a third etching treatment through the third mask, and is subjected to a third washing treatment, to obtain the first intermediate model; where, the first etching treatment and the second etching treatment are wet etching, and the third etching treatment is inductively coupled plasma etching. This is because most of pore structures are micro-nano pores, and the inductively coupled plasma etching is conducive to the formation of nano-scale matrix, and the combination of wet etching and inductively coupled plasma etching is conducive to both accuracy and efficiency.

The present disclosure does not limit the specific operation steps of the bonding treatment, and can adopt a conventional bonding method in the field. In some embodiments, the etched side of the first intermediate model is stacked with the glass cover to obtain a model to be bonded, and the model to be bonded is placed between two graphite sheets, and a steel plate or a corundum plate is placed on a side of the two graphite sheets away from the model to be bonded, and the model is then horizontally placed in a muffle furnace for the bonding treatment; where a temperature of the bonding treatment is 400-700° C. and time thereof is 4-12 h.

Where the specific size of the glass substrate and the glass cover are not limited in the present disclosure, and can be adjusted according to an actual situation. For example, in some embodiments, lengths and widths of the glass substrate and the glass cover are 4.5 cm respectively, and a total thickness of the glass substrate and the glass cover is 0.8-2 cm.

The introduction of the solutions into the second intermediate model is essentially the introduction of the solutions into the channel of the second intermediate model. In some embodiments, the first solution, the second solution and the third solution are introduced through an injection inlet sequentially. The injection inlet and a collection outlet are formed by a punching treatment and are respectively arranged on both opposite sides of the first intermediate model and are communicated with the channel. Where the punching treatment can be operated by equipment such as punching machine. The opening sizes of the injection inlet and collection outlet are related to the size of the glass substrate and can be determined according to an actual situation, for example, the opening sizes can be circular and have a diameter size of 2-3 mm.

The present disclosure does not limit a thickness of the calcium carbonate nanocrystalline layer, and for example, in some embodiments, the thickness of the calcium carbonate nanocrystalline layer is 0.5-4 μm.

By controlling the parameters such as amounts and the reaction time of the first solution, the second solution and the third solution, the packing density of $CaCO_3$ nanocrystalline on the microchannel surface can be adjusted, and thus the thickness of the calcium carbonate nanocrystalline layer can be adjusted, so as to control the surface roughness of the microchannel.

The micro-nanofluidic model of triple-medium carbonate reservoir prepared by the preparation method of the present disclosure can be directly used in a flooding experiment, which is helpful to understand a flow behavior of the triple-medium carbonate rock, especially a microscopic three-phase flow behavior of oil, gas and water under various conditions. The model of the present disclosure can withstand a pressure within 10 MPa of internal and external pressure difference, and can withstand a pressure of 70 MPa by cooperating with a confining pressure loading system; therefore, the model of the present disclosure can withstand harsh conditions of high temperature (300° C.) and high pressure (70 MPa), has a wide range of application and can meet the requirements of most reservoir environments.

The present disclosure is further described below through specific examples and comparative examples.

Example 1

Figure 2:
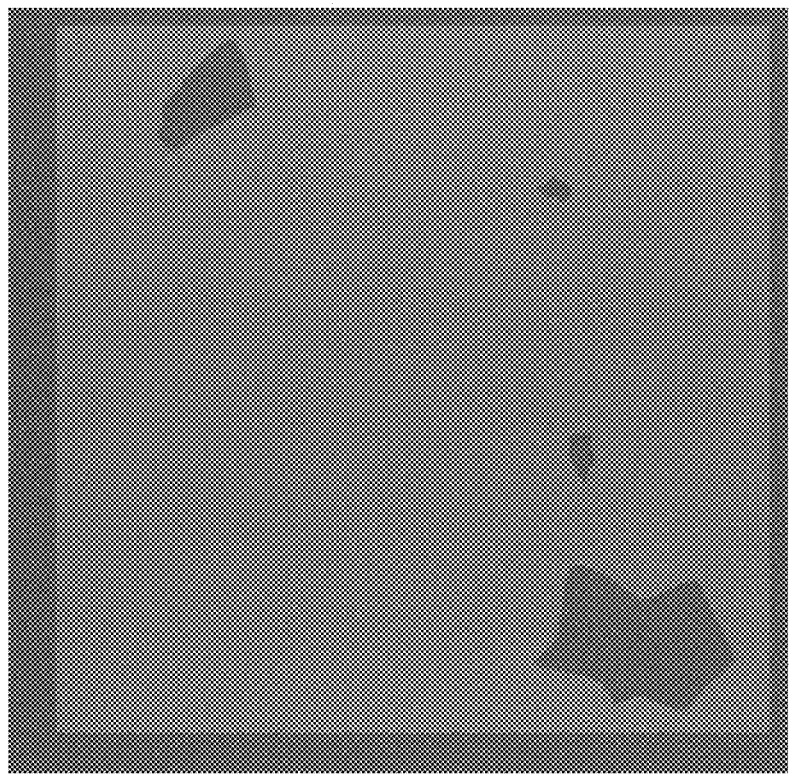
FIG. 2 is a front view of a first etched model of Example 1 of the present disclosure.
Figure 3:
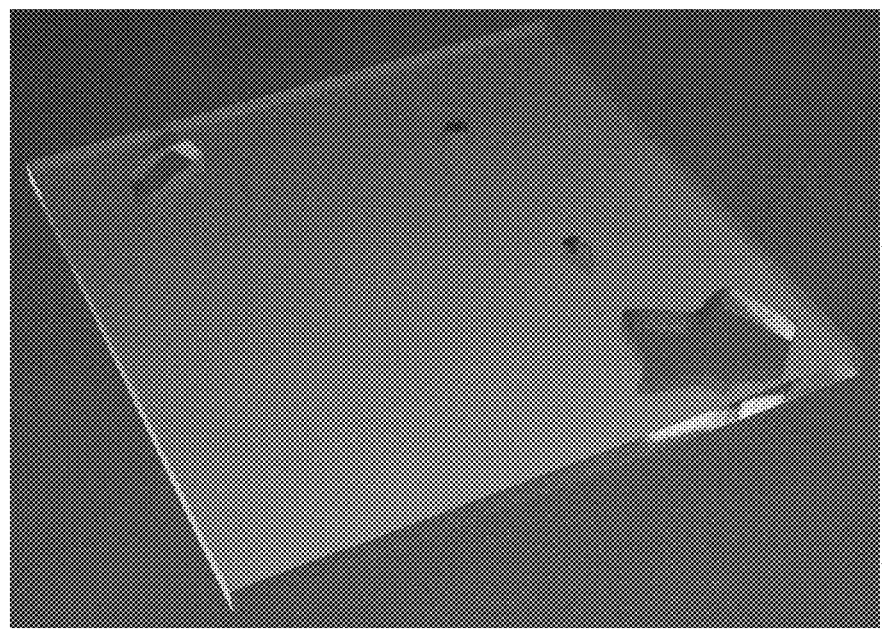
FIG. 3 is a perspective view of the first etched model in Example 1 of the present disclosure.
Figure 4:
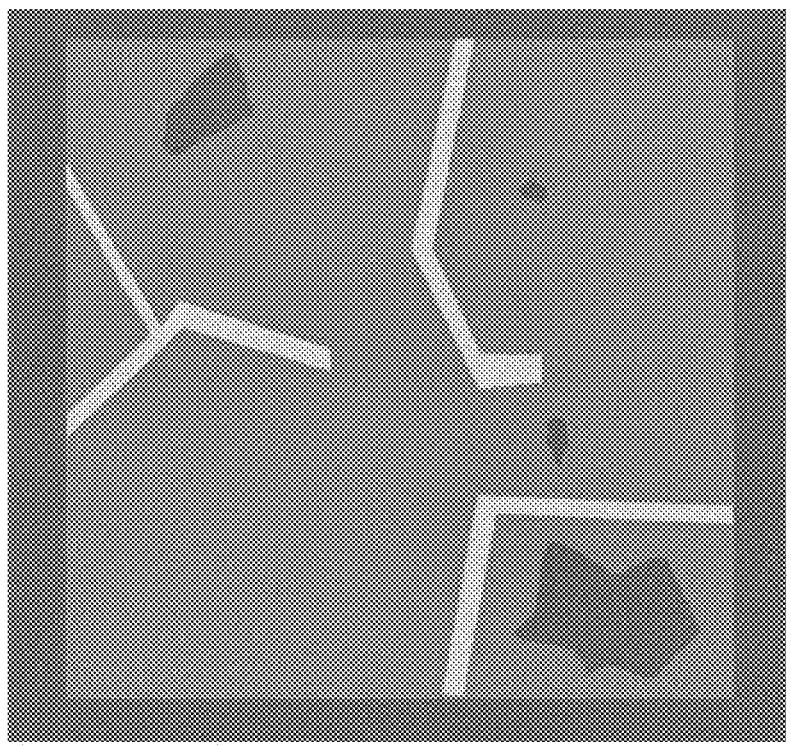
FIG. 4 is a front view of a second etched model of Example 1 of the present disclosure.
Figure 5:
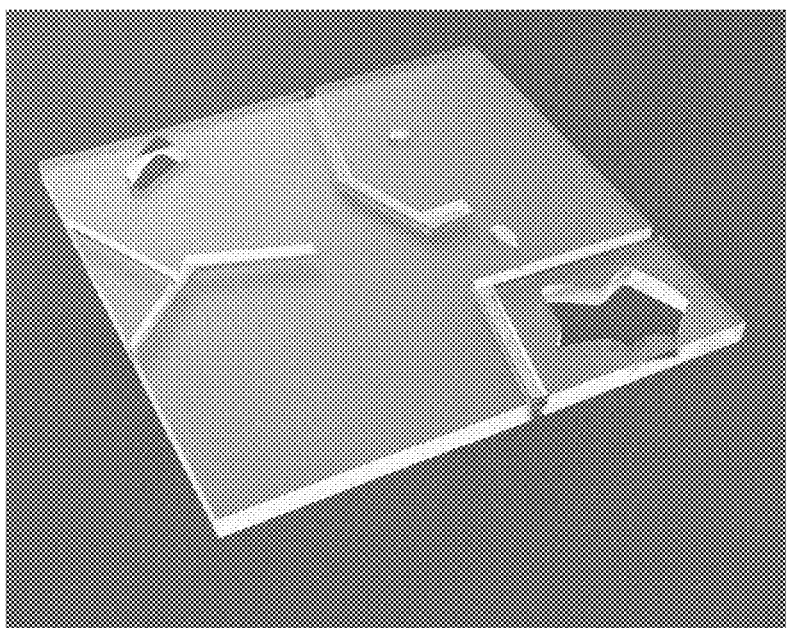
FIG. 5 is a perspective view of the second etched model in Example 1 of the present disclosure.
Figure 6:
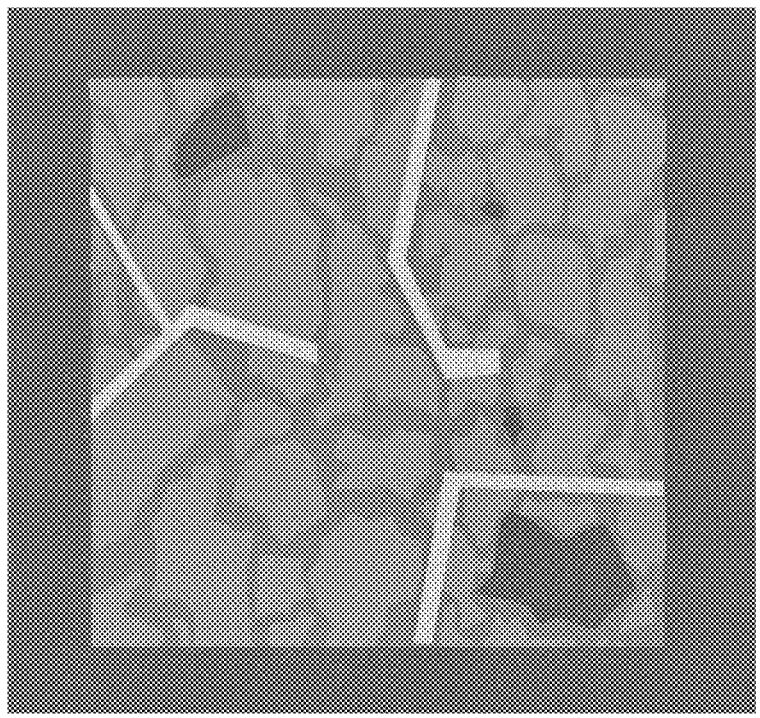
FIG. 6 is a front view of a first intermediate model of Example 1 of the present disclosure.
Figure 7:
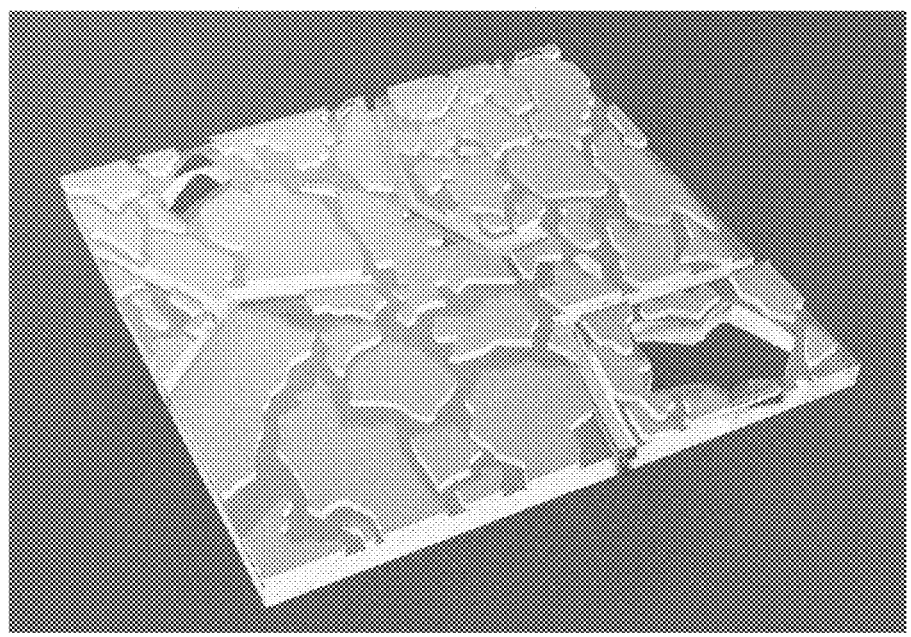
FIG. 7 is a perspective view of the first intermediate model in Example 1 of the present disclosure.
Figure 11:
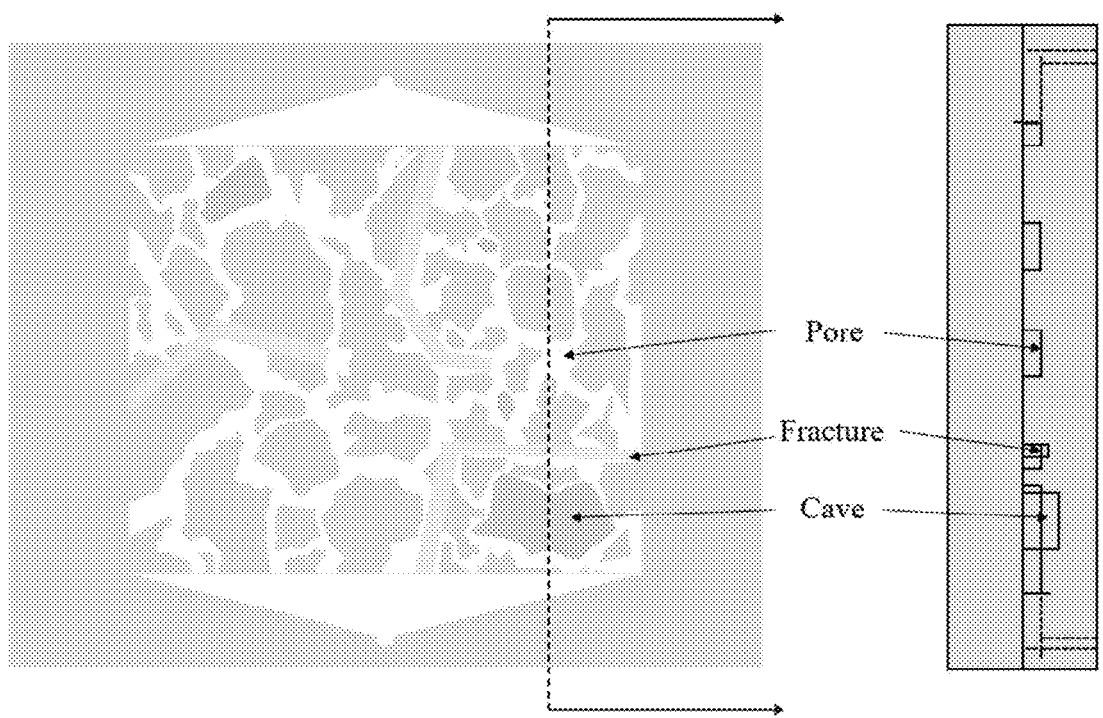
FIG. 11 is a top view (at left side) of a second intermediate model in Example 1 of the present disclosure and a cross-sectional view (at right side) corresponding to a position indicated by a dotted line.

A preparation method of micro-nanofluidic model of triple-medium carbonate reservoir includes the following steps:
- (1) a real carbonate reservoir in Shengli Oilfield was selected, and was scanned by micro-nano CT, thin section and scanning electron microscopy imaging techniques, to obtain a pore structure, a fracture structure and a cave structure from micron scale to nanometer scale;
- (2) based on the obtained three-dimensional data of the carbonate rock, a topological relationship of triple media, the pore structure, the fracture structure and the cave structure, was analyzed, and shapes and depths of the pore structure, the fracture structure and the cave structure were designed, and a three-dimensional structure of the carbonate rock and a communication relationship of the triple media were constructed; a first mask pattern, a second mask pattern and a third mask pattern were designed correspondingly, where the first mask pattern includes a pattern of the cave structure, the second mask pattern includes patterns of the fracture structure and the cave structure, and the third mask pattern includes patterns of the cave structure, the fracture structure and the pore structure;
- (3) patterns on the first mask pattern, the second mask pattern and the third mask pattern were transferred to a mask material to form a first mask, a second mask and a third mask; a first photoresist layer was formed on a glass substrate, and the first photoresist layer was subjected to a first exposure treatment and a first etching treatment through the first mask, and subjected to a first washing treatment, to obtain a first etched model (as shown in FIGS. 2 and 3); a second photoresist layer was formed on the first etched model, and the second photoresist layer was subjected to a second exposure treatment and a second etching treatment through the second mask, and subjected to a second washing treatment, to obtain a second etched model (as shown in FIGS. 4 and 5); a third photoresist layer was formed on the second etched model, and the third photoresist layer was subjected to a third exposure treatment and a third etching treatment through the third mask, and subjected to a third washing treatment, to obtain a first intermediate model (as shown in FIGS. 6 and 7); where the first etching treatment and the second etching treatment are wet etching, and the third etching treatment is inductively coupled plasma etching;
- (4) the etched side of the first intermediate model was fitted and aligned with a glass cover, air therein was discharged, and then moisture was removed by heating to get a model to be bonded; the model to be bonded was stacked between two graphite sheets, a steel plate or a corundum plate was placed on a side of the two graphite sheets away from the model to be bonded, and the model was horizontally placed in a muffle furnace for bonding treatment, so that a non-pattern area of the first intermediate model was closely bonded to the glass cover by bonding; after bonding, the stress was released by annealing, to obtain a second intermediate model (as shown in FIG. 11), where a temperature for bonding is 500° C. and time therefor is 5 hours;
- (5) the second intermediate model was taken out, and both ends of the first intermediate model were punched to form an injection inlet and a collection outlet, and a first solution, a second solution and a third solution were sequentially introduced through the injection inlet, to form a calcium carbonate nanocrystalline layer, and to a micro-nanofluidic model of triple-medium carbonate reservoir; where the first solution contains N-(trimethoxysilylpropyl) ethylenediamine triacetic acid sodium salt, the second solution contains $CaCl_2$, and the third solution contains $Na_2CO_3$.

Comparative Example 1

The preparation process of the present comparative example is basically the same as that of Example 1, except that steps (4) and (5) are omitted and the first intermediate model is directly used as a model of the present comparative example.

Ten sample models were prepared according to the above methods of Example 1 and Comparative example 1, and clean water was dropped onto the etched surfaces of the models, respectively, and contact angles between water droplets and the etched surfaces were measured. The test results are shown in FIGS. 9 (Example 1) and 10 (Comparative example 1).

Figure 9:
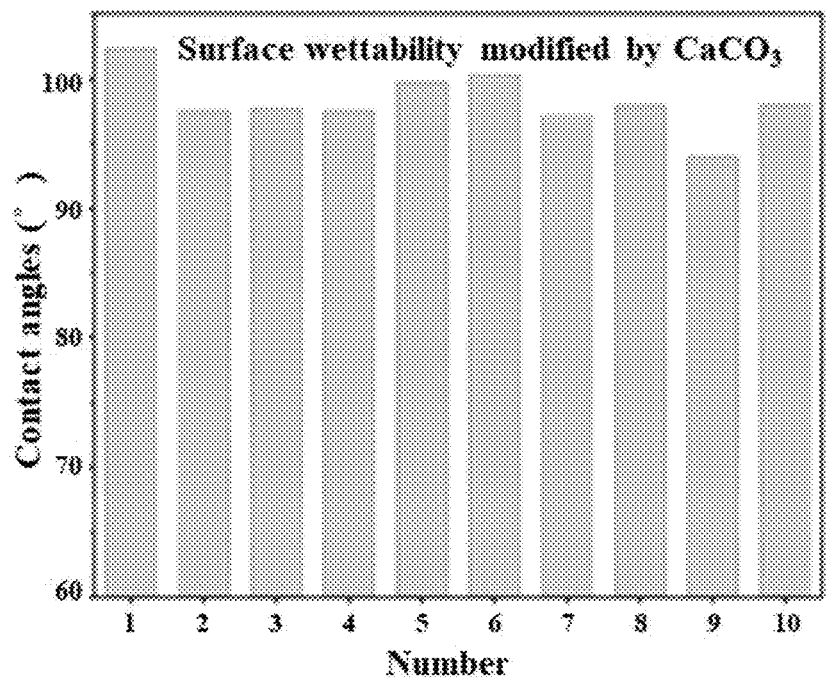
FIG. 9 is a bar graph of water contact angle of the model in Example 1 of the present disclosure.
Figure 10:
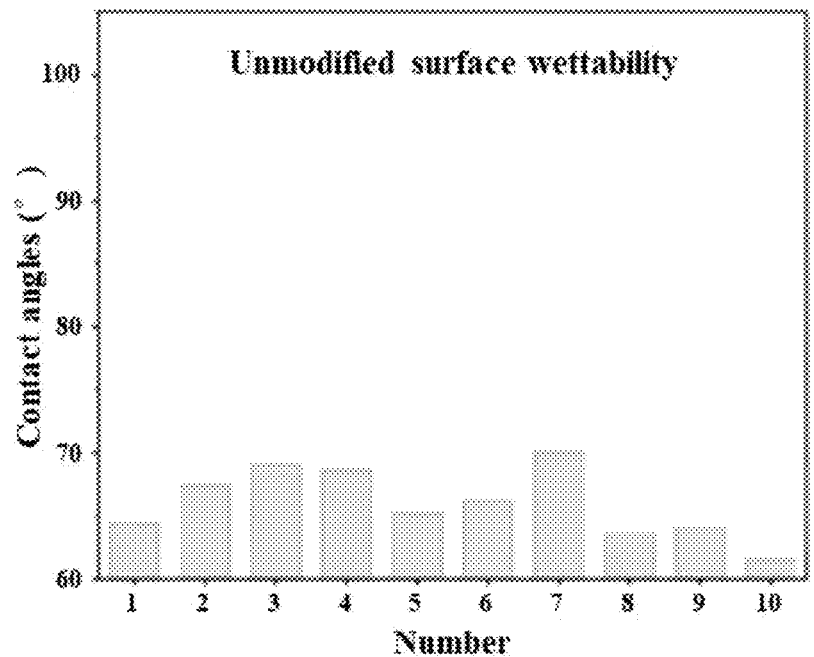
FIG. 10 is a bar graph of water contact angle of a model in Comparative example 1 of the present disclosure.

According to FIGS. 9 and 10, the present disclosure may make wettability of the models is closer to an actual carbonate reservoir by forming a calcium carbonate nanocrystalline layer on surfaces of microchannels, so that flow behaviors of oil and gas in this environment can be studied more accurately.

The present example provides the following ways to simulate the implementation of $CO_2$ sequestration using a triple-medium carbonate reservoir micro-nanofluidic model:
- Case 1: an oil-wet micro-nanofluidic model is saturated with a crude oil at reservoir temperature, and supercritical $CO_2$ is injected from the injection inlet, to simulate an injection well, a flow path of $CO_2$ is observed, and a fluid distribution is observed by an optical microscopy, to explore an influence of reservoir heterogeneity on $CO_2$ sequestration under influence of oil-wet.
- Case 2: a mixed-wet micro-nanofluidic model is placed at reservoir temperature and pressure and is saturated with a crude oil, and supercritical $CO_2$ is injected from the injection inlet, to simulate an injection well, a flow path of $CO_2$ is observed, and a fluid distribution is observed by an optical microscopy, to explore an influence of reservoir heterogeneity on $CO_2$ sequestration under influence of mixed-wet.

The concrete examples and experimental verification of the present disclosure are described in detail above. It should be understood that those skilled in the art can make many modifications and changes according to the idea of the present disclosure without creative work. Therefore, all technical solutions that can be obtained by those skilled in the art through logical analysis, reasoning or limited experiments on the basis of the prior art according to the idea of the present disclosure, should be within the scope of protection defined by the claims.

What is claimed is:

1. A preparation method of a micro-nanofluidic model of triple-medium carbonate reservoir, comprising the following steps:

obtaining a cave structure, a fracture structure and a pore structure of a carbonate rock, and preparing a first mask, a second mask and a third mask respectively; wherein the first mask has a cave structure of the reservoir, the second mask has the cave structure and a fracture structure of the reservoir, and the third mask has the cave structure, the fracture structure and a pore structure of the reservoir;

forming at least one photoresist layer on a glass substrate, and subjecting the at least one photoresist layer to an exposure treatment and an etching treatment through the first mask, the second mask and the third mask sequentially, so that etching depth at a position corresponding to the cave structure on the glass substrate is greater than etching depth at a position of the fracture structure, and the etching depth at the position of the fracture structure is greater than etching depth at a position of the pore structure, and subjecting the at least one photoresist layer to a washing treatment, to obtain a first intermediate model; wherein the position corresponding to the cave structure on the glass substrate is etched three times, the position of the fracture structure is etched twice, and the position of the pore structure is etched once; the method uses the etching treatment three times, the first two etchings are wet etchings, and the third etching is inductively coupled plasma etching;

stacking an etched side of the first intermediate model with a glass cover to obtain a model to be bonded, placing the model to be bonded between two graphite sheets, and placing a steel plate or a corundum plate on a side of the two graphite sheets away from the model to be bonded, and then horizontally placing into a muffle furnace for a bonding treatment, to obtain a second intermediate model; wherein the bonding treatment has a temperature of 400-700° C. and time of 4-12 hours; and introducing a first solution, a second solution and a third solution into the second intermediate model sequentially to form a calcium carbonate nanocrystalline layer and obtain the micro-nanofluidic model of triple-medium carbonate reservoir;

wherein the first solution comprises N-(trimethoxysilyl-propyl) ethylenediamine triacetic acid sodium salt, and the second solution comprises $Ca^{2+}$, and the third solution comprises $CO_3^{2-}$.

2. The preparation method according to claim 1, further comprising the following steps:

introducing a crude oil and water into the micro-nanofluidic model of triple-medium carbonate reservoir sequentially to undergo a flushing treatment, and subjecting to an aging and drying treatment, to change the model wettability from water-wet characteristic to oil-wet characteristic; or, introducing a paraffin solution, a crude oil and water into the micro-nanofluidic model of triple-medium carbonate reservoir sequentially to undergo a flushing treatment, and subjecting to an aging and drying treatment, to change the model wettability from water-wet characteristic to mixed-wet characteristic or oil-wet characteristic.

3. The preparation method according to claim 1, wherein the obtaining the cave structure, the fracture structure and the pore structure of the carbonate rock comprises the following steps:

selecting a triple-medium carbonate rock, washing oil and drying, to obtain a rock sample in cylindrical shape;

subjecting the rock sample to scanning image, to obtain the cave structure and the fracture structure of the carbonate rock;

obtaining the pore structure of the rock sample by a thin section and a scanning electron microscopy.

4. The preparation method according to claim 1, wherein before applying photoresist on the glass substrate, the preparation method further comprises the following steps: placing the glass substrate into a solution comprising a surfactant to undergo an ultrasonic treatment.

5. The preparation method according to claim 1, wherein the forming the at least one photoresist layer on the glass substrate, and subjecting the at least one photoresist layer to the exposure treatment and the etching treatment through the first mask, the second mask and the third mask sequentially, and subjecting the at least one photoresist layer to the washing treatment, to obtain the first intermediate model comprises:

forming a first photoresist layer on the glass substrate, and subjecting the first photoresist layer to a first exposure treatment and a first etching treatment through the first mask, and then subjecting to a first washing treatment, to obtain a first etched model;

forming a second photoresist layer on the first etched model, and subjecting the second photoresist layer to a second exposure treatment and a second etching treatment through the second mask, and then subjecting to a second washing treatment, to obtain a second etched model; and forming a third photoresist layer on the second etched model, and subjecting the third photoresist layer to a third exposure treatment and a third etching treatment through the third mask, and then subjecting to a third washing treatment, to obtain the first intermediate model, wherein the first etching treatment and the second etching treatment each are wet etchings, and the third etching treatment is inductively coupled plasma etching.

6. The preparation method according to claim 1, further comprising:

subjecting to a punching treatment at both ends of the first intermediate model to form an injection inlet and a collection outlet.

7. The preparation method according to claim 6, further comprising the following steps: introducing the first solution, the second solution and the third solution sequentially through the injection inlet.

8. The preparation method according to claim 1, wherein the calcium carbonate nanocrystalline layer has a thickness of 0.5-4 μm.

9. The preparation method according to claim 1, wherein the at least one photoresist layer comprises at least two layers.

* * * * *